United States Patent
Watanabe et al.

(10) Patent No.: US 10,900,602 B2
(45) Date of Patent: Jan. 26, 2021

(54) CABLE

(71) Applicant: Hitachi Metals, Ltd., Tokyo (JP)

(72) Inventors: Takanobu Watanabe, Hitachi (JP); Detian Huang, Hitachi (JP); Haruyuki Watanabe, Hitachi (JP); Kimika Kudo, Kitaibaraki (JP)

(73) Assignee: HITACHI METALS, LTD., Tokyo (JP)

( * ) Notice: Subject to any disclaimer, the term of this patent is extended or adjusted under 35 U.S.C. 154(b) by 285 days.

(21) Appl. No.: 15/720,047

(22) Filed: Sep. 29, 2017

(65) Prior Publication Data
US 2018/0100614 A1 Apr. 12, 2018

(30) Foreign Application Priority Data
Oct. 11, 2016 (JP) .................... 2016-200293

(51) Int. Cl.
| | |
|---|---|
| F16L 53/00 | (2018.01) |
| H05B 3/08 | (2006.01) |
| H05B 3/56 | (2006.01) |
| F16L 53/38 | (2018.01) |
| A61B 8/00 | (2006.01) |
| F28F 1/36 | (2006.01) |
| A61B 1/00 | (2006.01) |
| A61B 1/12 | (2006.01) |

(52) U.S. Cl.
CPC ............ *F16L 53/38* (2018.01); *A61B 8/4444* (2013.01); *H05B 3/08* (2013.01); *H05B 3/56* (2013.01); *A61B 1/00114* (2013.01); *A61B 1/12* (2013.01); *A61B 8/546* (2013.01); *F28F 1/36* (2013.01)

(58) Field of Classification Search
CPC . F16L 53/34; F16L 53/35; F16L 53/37; F16L 53/38; H05B 3/08; H05B 3/54; H05B 3/56; H05B 3/60; G01S 7/52079
USPC ........... 219/540–544; 338/226; 600/437–472
See application file for complete search history.

(56) References Cited

U.S. PATENT DOCUMENTS

| | | | | |
|---|---|---|---|---|
| 3,970,821 A | * | 7/1976 | Crandell | B22D 17/2272 |
| | | | | 219/523 |
| 4,822,980 A | * | 4/1989 | Carbone | H05B 3/141 |
| | | | | 219/205 |
| 8,376,950 B2 | * | 2/2013 | Nagano | A61B 8/12 |
| | | | | 600/459 |

(Continued)

FOREIGN PATENT DOCUMENTS

| | | |
|---|---|---|
| JP | H09-140706 A | 6/1997 |
| JP | 2016-123536 A | 7/2016 |
| WO | WO 2014/076973 A1 | 5/2014 |

OTHER PUBLICATIONS

Japanese Office Action, dated Jul. 14, 2020, in Japanese Patent Application No. 2016-200293 and English Translation thereof.

*Primary Examiner* — Justin C Dodson
(74) *Attorney, Agent, or Firm* — McGinn I. P. Law Group, PLLC

(57) ABSTRACT

A cable includes a bush that accommodates a coil formed by helically winding a heat-transfer wire to have a heat dissipation function. The bush may include a resin material including a heat-transfer powder mixed therein. The heat-transfer wire may be configured to be connected to a heat source attached to the cable to receive heat from the heat source. The bush may include a smooth surface.

13 Claims, 2 Drawing Sheets

(56) References Cited

U.S. PATENT DOCUMENTS

| | | | |
|---|---|---|---|
| 2006/0100513 A1* | 5/2006 | Hashimoto | A61B 8/00 600/437 |
| 2008/0243002 A1* | 10/2008 | Munce | A61B 5/0095 600/459 |
| 2008/0312537 A1* | 12/2008 | Hyuga | B06B 1/0622 600/459 |
| 2009/0030325 A1* | 1/2009 | Hyuga | A61B 1/05 600/459 |
| 2015/0253290 A1 | 9/2015 | Fujii et al. | |

* cited by examiner

CABLE

The present application is based on Japanese patent application No. 2016-200293 filed on Oct. 11, 2016, the entire contents of which are incorporated herein by reference.

BACKGROUND OF THE INVENTION

1. Field of the Invention

The invention relates to a cable having a bush at one end.

2. Description of the Related Art

An ultrasonograph is provided with an ultrasonic probe (ultrasound probe or echo probe, hereinafter, also simply referred to as "probe") and a control unit. The prove is provided with a piezoelectric portion having a piezoelectric element and an integrated circuit (IC) and a cable attached to the piezoelectric portion, and is configured that the piezoelectric portion and a portion of the cable is housed in a housing (see e.g. JP 2016/123536).

SUMMARY OF THE INVENTION

When the ultrasonograph is fed with electricity, the piezoelectric portion is activated so as to generate heat. To dissipate the heat of the piezoelectric portion out of the probe, the housing is configured to be able to dissipate heat from the surface thereof, or a shield provided inside the housing is configured to have a heat dissipation function. However, heat dissipation by such configurations is sometimes not enough, which may results in that the housing is heated and an examined person may get burnt.

It is an object of the invention to provide a cable that functions to achieve heat dissipation of the ultrasonic probe.

According to an embodiment of the invention, a cable comprises a bush that accommodates a coil formed by helically winding a heat-transfer wire to have a heat dissipation function.

Effects of the Invention

According to an embodiment of the invention, an ultrasonic probe cable can be provided that functions to achieve heat dissipation of the ultrasonic probe.

BRIEF DESCRIPTION OF THE DRAWINGS

Next, the present invention will be explained in more detail in conjunction with appended drawings, wherein.

DETAILED DESCRIPTION OF THE PREFERRED EMBODIMENTS

Embodiment of the Invention (1) Configuration of Ultrasonic Probe

The configuration of an ultrasonic probe will be described in reference to FIGS. 1A and 1B.

Figure 1A:
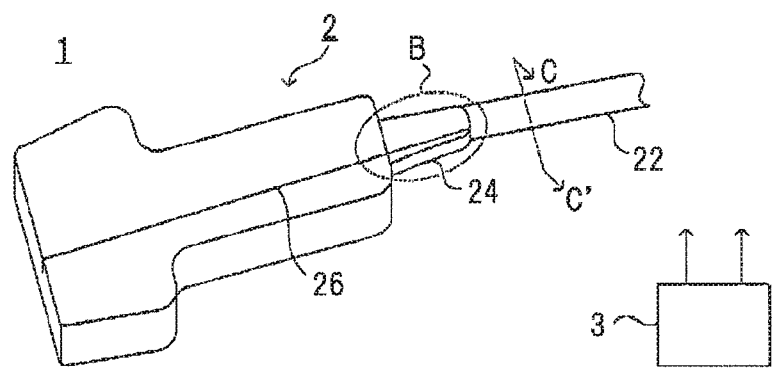
FIG. 1A is an exemplary schematic diagram illustrating an ultrasonograph having a cable in an embodiment of the present invention.

As shown in FIG. 1A, an ultrasonograph 1 has a probe 2 and a control unit 3. As shown in FIG. 1B, the probe 2 has a cable 22 and a housing 23. The cable 22 is attached (connected) to a piezoelectric portion 21 at one end and connected to the control unit 3 at the other end. The housing 23 houses the piezoelectric portion 21 and a portion of the cable 22 and is to be a grip portion which is gripped by an operator. The piezoelectric portion 21 has a piezoelectric element and an integrated circuit (IC chip) which converts ultrasonic wave received from the piezoelectric element into an electrical signal. The cable 22 is configured so that electrical signals can be transmitted between the piezoelectric portion 21 and the control unit 3. The housing 23 has an opening formed to expose a surface of the piezoelectric portion 21 housed in the housing 23, and the piezoelectric portion 21 exposed from the opening is brought into contact with a measuring object (e.g., human body). The ultrasonograph 1 is configured that ultrasonic wave obtained by contact between the piezoelectric portion 21 and the measuring object is converted into an electrical signal in the piezoelectric portion 21, the electrical signal is sent to the control unit 3 through the cable 22, and the control unit 3 performs information processing and image processing, etc.

(2) Configuration of the Cable

A cable with a bush is used as the cable 22. Next, the configuration of the cable with a bush will be described in reference to the drawings.

Figure 1B:
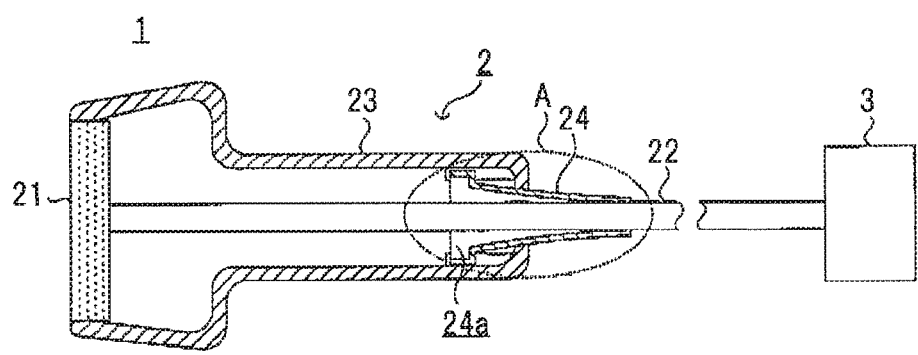
FIG. 1B is an exemplary schematic cross sectional view showing the ultrasonograph in FIG. 1A.

As shown in FIGS. 1A and 1B, a bush (cable bush) 24 is attached to one end of the cable 22 in the present embodiment. To attach the bush 24, the cable 22 is inserted through a through-hole 24a formed on the bush 24.

The bush 24 is provided to restrict the cable 22 so that a bend radius (radius of curvature) of the cable 22 in the vicinity of the base end of the housing 23 (e.g., a portion circled by the dotted line B in FIG. 1A) does not become smaller than a predetermined threshold when the cable 22 is moved. The reason is as follows: when the cable 22 is moved, the cable 22 is bent very frequently in the vicinity of the base end of the housing 23 and the bending of the cable 22 at such portion is often a very sharp curve with a very small bend radius. Therefore, the bush 24 is provided and the cable 22 thus can be prevented from breaking due to bending.

The bush 24 is preferably formed of a resin material to which heat-transfer powder is mixed. The heat-transfer powder which can be suitably used here is, e.g., alumina ($Al_2O_3$) powder. The resin material which can be suitably used here is, e.g., polyvinyl chloride (PVC) or silicone rubber.

The surface of the bush 24 is preferably smooth. In other words, the bush 24 preferably does not have any recess (groove) on the surface.

Figure 2:
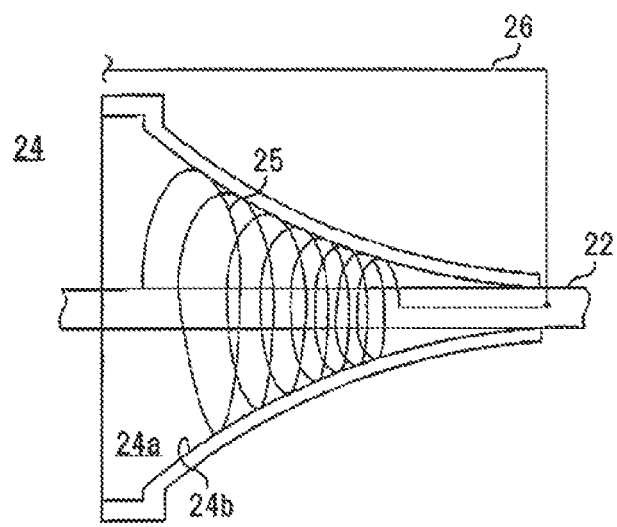
FIG. 2 is an exemplary enlarged view showing a portion circled by the dotted line A in FIG. 1B.

As shown in FIG. 2, a coil 25 formed by helically (spirally) winding a heat-transfer wire is accommodated inside the bush 24 (inside the through-hole 24a).

The coil 25 has properties of being deformed according to a force applied to the coil 25 and returning to the original shape upon removal of the force applied to the coil 25, i.e., spring properties. This allows the bush 24 to follow the movement of the cable 22. In other words, the bush 24 can have sufficient following capability. In addition, even if the bush 24 is repeatedly bent, an ability of the bush 24 to return to the original shape (non-bent shape) on its own when the force applied to the bush 24 is removed can be ensured for a long period of time. In other words, the bush 24 can have sufficient flex resistance.

The coil 25 is provided inside the through-hole 24a formed on the bush 24 so as to surround the cable 22 inserted through the through-hole 24a. In addition, the coil 25 is preferably in contact with an inner wall 24b of the bush 24.

The heat-transfer wire is a wire (wire rod) through which heat generated by, e.g., the piezoelectric portion 21 can be conducted to the bush 24. The heat-transfer wire has excellent heat conductance (high thermal conductivity) and preferably has high strength (tensile strength) for further increasing following capability and flex resistance of the bush 24. As such heat-transfer wire, it is possible to use a copper wire or a copper alloy wire. The copper wire is more preferable than the copper alloy wire in view of high thermal conductivity, while the copper alloy wire is more preferable than the copper wire in view of high strength.

The coil 25 is connected, through a heat-transfer wire 26 such as copper wire, to a heat source (e.g., the piezoelectric portion 21) attached to the cable 22 and receives heat from the heat source. The heat-transfer wire 26 provides a new heat dissipation path which is different from conventional heat dissipation paths, such as the surface of the housing 23 and a shield provided inside the housing 23, of the probe 2. In other words, the heat-transfer wire 26 functions as a bypass route for heat conduction from the heat source. The heat-transfer wire 26 can be, e.g., the same heat-transfer wire as that constituting the coil 25. The heat-transfer wire 26 may be the same wire as the heat-transfer wire constituting the coil 25 or may be a different wire. The heat-transfer wire 26 is provided, e.g., to run on the outer surface of the housing 23, as shown in FIG. 1A.

Figure 3:
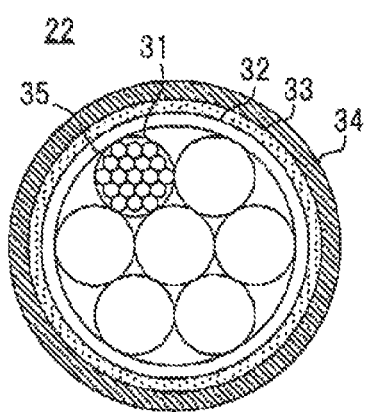
FIG. 3 is a cross sectional view showing a structure of the cable of the ultrasonograph taken along a line C-C in FIG. 1A.

As the cable 22, it is possible to use a cable provided with, e.g., core units 31, a binding tape 32, a shield 33 and a sheath 34, as shown in FIG. 3. The core unit 31 is formed by twisting plural coaxial cables 35, etc., which can transmit electrical signals. The coaxial cable is, e.g., a cable having an inner conductor to be a transmission path of the electrical signal, an insulation layer provided around the inner conductor, an outer conductor provided around the insulation layer and serving as a shield, and an outer cover (jacket) provided around the outer conductor. The binding tape 32 is to bundle a twisted wire formed by twisting the plural core units 31, and is formed of a resin tape of polytetrafluoroethylene (PTFE), etc. The shield 33 is provided to surround (cover) the plural core units 31 (or the binding tape 32 when provided). As the shield 33, it is possible to use, e.g., a braided shield formed by braiding copper-containing strands (e.g., copper wires), etc. The sheath 34 is formed of, e.g., a medical insulating resin. The medical insulating resin, also called medical resin or medical grade resin, is a biocompatible (highly biologically compatible) resin which is non-toxic and does not cause allergic symptoms such as inflammation upon contact with living organisms. As such medical insulating resin, it is possible to use, e.g., a medical grade PVC (polyvinyl chloride).

(3) Effects of the Embodiment

One or more effects below are obtained in the present embodiment.

(a) Since the bush 24 has a heat dissipation function by accommodating the coil 25 formed of a heat-transfer wire, heat generated by the piezoelectric portion 21 as a heat source in the probe 2 can be received by the bush 24 and then dissipated to the outside of the bush 24 (the probe 2). In other words, it is possible to assist (help) heat dissipation of the probe 2. As a result, it is possible to prevent the housing 23 as a grip portion for an operator from being heated during use of the ultrasonograph 1.

It could be configured that heat from the heat source is received by, e.g., the shield 33 of the cable 22 without configuring the bush 24 to have a heat dissipation function. However, since the thick sheath 34 (e.g., 0.5 mm to 1 mm) is provided around the shield 33 as described above, there is a problem that heat received by the shield 33 is not easily dissipated to the outside of the cable 22. Particularly when a gap is formed between the shield 33 and the sheath 34, heat is likely to be accumulated in the gap and the problem becomes prominent.

(b) Since the bush 24 has a heat dissipation function, it is possible to realize further downsizing of the probe 2 and also possible to display higher-quality images on a display portion of the ultrasonograph 1.

The reason is as follows: when the housing 23 having a smaller size is provided for downsizing of the probe 2, the surface area of the housing 23 is reduced, and as a result, the amount of heat dissipated from the surface of the housing 23 is also reduced. However, since the bush 24 has a heat dissipation function, heat dissipation reduced by downsizing of the probe 2 can be assisted by the bush 24, and the amount of heat which can be dissipated is equivalent to or more than before the downsizing of the probe 2. The downsizing of the probe 2, which is difficult in the conventional technique, can be thereby realized.

Meanwhile, in recent years, the images displayed on the display portion are required to be higher quality. There are requirements of, e.g., a further increase in resolution of the images, 3D or animation display of the images and beam-forming control at the piezoelectric portion 21. When the quality of the images is increased, heat generation by the piezoelectric portion 21 increases. Even in such a case, the heat dissipation amount of the entire probe 2 can be increased to more than the conventional probe by configuring the bush 24 to have a heat dissipation function. Therefore, the heat generated by the piezoelectric portion 21 can be reliably dissipated to the outside of the probe 2.

(c) The heat dissipation capability of the bush 24 can be further enhanced by using a resin material mixed with heat-transfer powder to form the bush 24.

In general, the bush 24 formed of the resin material mixed with heat-transfer powder described above is more brittle (has lower strength) than a bush formed of a resin material not mixed with heat-transfer powder, and the bush 24 thus has lower flex resistance. However, since the bush 24 accommodates the coil 25 in the present embodiment, the bush 24 having a low flex resistance due to mixing the heat-transfer powder can be reinforced. As a result, the bush 24 can have a predetermined flex resistance even when the bush 24 is formed of a resin material mixed with heat-transfer powder. It is possible to ensure to have flex resistance which is, e.g., equivalent to or more than the bush formed of a resin material not mixed with heat-transfer powder.

(d) Since the coil 25 is in contact with the inner wall 24b of the bush 24, heat received by the coil 25 can be efficiently dissipated to the outside of the bush 24 through the heat-transfer powder.

(e) Since the bush 24 has a smooth surface and thus has a smaller surface area than when a recess is formed on the surface, it is possible to reduce the amount of dust adhered to the bush 24. In addition, it is easier to remove (clean) the dust adhered to the surface of the bush 24 than when a recess is formed on the surface. Due to such configuration, the cable 22 with the bush 24 in the present embodiment can be suitably used for a medical apparatus (medical device) such as the ultrasonograph 1.

(f) The cable 22 in the present embodiment is particularly effective when a user needs to grip the probe 2, etc., with a heat source.

Other Embodiments of the Invention

Although the embodiment of the invention has been specifically described, the invention is not to be limited to the embodiment and can be appropriately changed without departing from the gist thereof.

Although the example in which the coil 25 is accommodated in the bush 24 has been described in the embodiment, it is not limited thereto. For example, a braided member formed by braiding plural heat-transfer wires may be accommodated in the bush 24. This also allows the bush 24 to have a heat dissipation function and it is possible to obtain the same effects as the above-described embodiment. However, use of the coil 25 is more preferable than the braided member since following capability and flex resistance of the bush 24 can be increased.

Although the example in which the heat source (the piezoelectric portion 21) is connected to the coil 25 through the heat-transfer wire 26 provided on the outer surface of the housing 23 has been described in the embodiment, it is not limited thereto. For example, the shield provided inside the housing 23 and having a heat dissipation function may be connected to the coil 25 inside the housing 23. This also achieves the same effects as the above-described embodiment.

PREFERRED EMBODIMENTS OF THE INVENTION

Preferred embodiments of the invention will be described below.

[1] An aspect of the invention provides a cable comprising a bush that accommodates a coil formed by helically winding a heat-transfer wire to have a heat dissipation function.

[2] Another aspect of the invention provides a cable comprising a bush that accommodates a braided member formed by braiding plural heat-transfer wires to have a heat dissipation function.

[3] The cable defined by [1] or [2] may be configured such that the bush comprises a resin material including a heat-transfer powder mixed therein.

[4] The cable defined by any one of [1] to [3] may be configured such that the heat-transfer wire (the coil or the braided member) is connected to a heat source attached to the cable to receive heat from the heat source.

[5] The cable defined by any one of [1] to [4] may be configured such that the bush comprises a smooth surface.

[6] The cable defined by any one of [1] to [5] may be used for an ultrasonic probe.

What is claimed is:

1. A probe, comprising:
a bush that accommodates a coil formed by helically winding a heat-transfer wire to have a heat dissipation function; and
a cable that passes through an axial direction of the bush,
wherein an inner wall of the bush has a tapered shape which continuously changes in diameter, and the heat-transfer wire is wound in a manner that corresponds to the tapered shape of the inner wall by being continuously changed in a winding diameter to follow the tapered shape of the bush inner wall,
wherein the bush comprises a resin material including a heat-transfer powder mixed therein, the heat-transfer powder being configured to dissipate heat, which is received from the heat-transfer wire, outside of the bush, and
wherein the coil is in a direct contact with the inner wall of the bush.

2. The probe according to claim 1, wherein the heat-transfer wire is configured to be connected to a heat source attached to the probe to receive heat from the heat source.

3. The probe according to claim 1, wherein the bush comprises a smooth surface.

4. An ultrasonic probe, comprising the probe according to claim 1.

5. The probe according to claim 2, wherein the bush comprises a smooth surface.

6. An ultrasonic probe, comprising the probe according to claim 2.

7. An ultrasonic probe, comprising the probe according to claim 3.

8. The probe according to claim 1, wherein the resin material comprises one of polyvinyl chloride (PVC) and a silicone rubber.

9. The probe according to claim 1, wherein the heat-transfer powder comprises alumina.

10. The probe according to claim 1, wherein the winding diameter of the heat-transfer wire continuously reduces from an end surface of the heat-transfer wire to another end surface of the heat-transfer wire.

11. The probe according to claim 1, wherein the heat-transfer wire is wound around the cable.

12. The probe according to claim 1, wherein the coil has spring properties such that the coil is configured to be deformed according to a force applied to the coil and returning to an original shape upon removal of the force applied to the coil.

13. A probe, comprising:
a bush that accommodates a coil formed by helically winding a heat-transfer wire to have a heat dissipation function; and
a cable that passes through an axial direction of the bush,
wherein an inner wall of the bush has a tapered shape which continuously changes in diameter, and the heat-transfer wire is wound in a manner that corresponds to the tapered shape of the inner wall by being continuously changed in a winding diameter to follow the tapered shape of the inner wall,
wherein the bush comprises a resin material including a heat-transfer powder mixed therein, the heat-transfer powder being configured to dissipate heat, which is received from the heat-transfer wire, outside of the bush, and
wherein the heat-transfer wire is wound around the cable.

* * * * *